US009308301B2

(12) United States Patent
Askari et al.

(10) Patent No.: US 9,308,301 B2
(45) Date of Patent: Apr. 12, 2016

(54) NON-DEGRADABLE, LOW SWELLING, WATER SOLUBLE RADIOPAQUE HYDROGEL POLYMER

(75) Inventors: Syed H. Askari, San Jose, CA (US); Robert G. Whirley, Santa Rosa, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 1278 days.

(21) Appl. No.: 13/089,960

(22) Filed: Apr. 19, 2011

(65) Prior Publication Data
US 2011/0196060 A1  Aug. 11, 2011

Related U.S. Application Data

(63) Continuation of application No. 11/097,467, filed on Apr. 1, 2005, now abandoned.

(51) Int. Cl.
| A61K 51/00 | (2006.01) |
| A61M 36/14 | (2006.01) |
| A61L 31/14 | (2006.01) |
| A61L 24/00 | (2006.01) |
| A61L 31/18 | (2006.01) |
| A61K 49/04 | (2006.01) |

(52) U.S. Cl.
CPC .......... *A61L 31/145* (2013.01); *A61K 49/0457* (2013.01); *A61L 24/0031* (2013.01); *A61L 31/18* (2013.01); *A61K 49/0404* (2013.01); *A61L 2430/36* (2013.01)

(58) Field of Classification Search
USPC ....................................................... 424/1.25
See application file for complete search history.

(56) References Cited

U.S. PATENT DOCUMENTS

| 3,631,854 | A | 1/1972 | Fryer |
| 5,191,033 | A | 3/1993 | Cuscurida et al. |
| 5,221,726 | A | 6/1993 | Dabi et al. |
| 5,350,784 | A | 9/1994 | Darwen et al. |
| 5,370,691 | A | 12/1994 | Samson |
| 5,423,851 | A | 6/1995 | Samuels |
| 5,438,109 | A | 8/1995 | Nugent, Jr. et al. |
| 5,470,911 | A | 11/1995 | Rhee et al. |
| 5,476,666 | A | 12/1995 | Rhee et al. |
| 5,489,630 | A | 2/1996 | Walker |
| 5,507,770 | A | 4/1996 | Turk |
| 5,510,121 | A | 4/1996 | Rhee et al. |
| 5,510,418 | A | 4/1996 | Rhee et al. |
| 5,524,633 | A | 6/1996 | Heaven et al. |
| 5,529,653 | A | 6/1996 | Glastra |
| 5,534,024 | A | 7/1996 | Rogers et al. |
| 5,543,486 | A | 8/1996 | Abe et al. |
| 5,548,026 | A | 8/1996 | Jorissen et al. |
| 5,554,185 | A | 9/1996 | Block et al. |
| 5,567,748 | A | 10/1996 | Klein et al. |
| 5,567,782 | A | 10/1996 | Marten et al. |
| 5,585,446 | A | 12/1996 | Marten et al. |
| 5,587,409 | A | 12/1996 | Dreischhoff et al. |
| 5,599,855 | A | 2/1997 | Walker |
| 5,604,269 | A | 2/1997 | Papalos et al. |
| 5,623,046 | A | 4/1997 | Papalos et al. |
| 5,744,545 | A | 4/1998 | Rhee et al. |
| 5,786,421 | A | 7/1998 | Rhee et al. |
| 5,847,027 | A | 12/1998 | Marten et al. |
| 5,854,312 | A | 12/1998 | Klippstein |
| 5,871,537 | A | 2/1999 | Holman et al. |
| 5,906,864 | A | 5/1999 | Osterhold et al. |
| 5,908,864 | A | 6/1999 | Casey |
| 5,936,035 | A | 8/1999 | Rhee et al. |
| 5,963,011 | A | 10/1999 | Haller et al. |
| 5,980,570 | A | 11/1999 | Simpson |
| 6,036,640 | A | 3/2000 | Corace et al. |
| 6,060,534 | A | 5/2000 | Ronan et al. |
| 6,143,015 | A | 11/2000 | Nobles |
| 6,168,614 | B1 | 1/2001 | Andersen et al. |
| 6,245,835 | B1 | 6/2001 | Klein et al. |
| 6,294,596 | B1 | 9/2001 | Papalos et al. |
| 6,312,462 | B1 | 11/2001 | McDermott et al. |
| 6,319,276 | B1 | 11/2001 | Holman et al. |
| 6,338,869 | B1 | 1/2002 | Nakano et al. |
| 6,395,019 | B2 | 5/2002 | Chobotov |
| 6,534,560 | B2 | 3/2003 | Loomis et al. |
| 6,675,971 | B2 | 1/2004 | Case |
| 6,706,064 | B1 | 3/2004 | Anson |
| 6,746,623 | B2 | 6/2004 | Slone et al. |
| 6,773,754 | B2 | 8/2004 | Whiter |
| 6,818,018 | B1 | 11/2004 | Sawhney |
| 6,858,299 | B2 | 2/2005 | Lundquist et al. |

(Continued)

FOREIGN PATENT DOCUMENTS

| EP | 0 441 516 B1 | 8/1991 |
| EP | 0 617 930 A1 | 10/1994 |

(Continued)

OTHER PUBLICATIONS

International Search Report for International Application No. PCT/US2006/011140, mailed on Jan. 31, 2007.
International Preliminary Report on Patentability for International Application No. PCT/US2006/011140, issued on Oct. 3, 2007.
WPI/Thomson, 1991-181461 XP-002414652 dated May 9, 1991.
Greenwald et al., "Highly Water Soluble Taxol Derivatives: 7-Polyethylene Glycol Carbamates and Carbonates", J. Org. Chem., 1995, 60 (2), pp. 331-336.
Harris, J.M., "Laboratory Synthesis of Polyethylene Glycol Derivatives", JMS-REV. Macromol. Chem. Phys., 1985, C25(3), pp. 325-373.
Harris, J.M., "Introduction to Biotechnical and Biomedical Applications of Poly(Ethylene Glycol)", in Poly(Ethylene Glycol) Chemistry: Biotechnical and Biomedical Applications, edited by J. Milton Harris, Plenum Press, New York, 1992, pp. 1-14.

(Continued)

*Primary Examiner* — Michael G Hartley
*Assistant Examiner* — Melissa Perreira
(74) *Attorney, Agent, or Firm* — Hoffmann & Baron, LLP

(57) ABSTRACT

Hydrogel compositions prepared from amine components and glycidyl ether components are provided which are biocompatible and suitable for use in vivo due, in part, to their excellent stability.

42 Claims, No Drawings

(56) References Cited

U.S. PATENT DOCUMENTS

| | | |
|---|---|---|
| 6,958,212 B1 | 10/2005 | Hubbell et al. |
| 7,008,979 B2 | 3/2006 | Schottman et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,632,291 B2 | 12/2009 | Stephens et al. |
| 7,744,912 B1 | 6/2010 | Hubbell et al. |
| 7,766,954 B2 | 8/2010 | Chobotov et al. |
| 2002/0010231 A1 | 1/2002 | Shirakawa et al. |
| 2003/0074058 A1 | 4/2003 | Sherry |
| 2003/0120338 A1 | 6/2003 | Chobotov et al. |
| 2003/0125797 A1 | 7/2003 | Chobotov et al. |
| 2003/0208831 A1 | 11/2003 | Lazar et al. |
| 2003/0225453 A1 | 12/2003 | Murch |
| 2004/0176836 A1 | 9/2004 | Kari et al. |
| 2004/0254625 A1 | 12/2004 | Stephens et al. |
| 2005/0158272 A1 | 7/2005 | Whirley et al. |
| 2006/0025854 A1 | 2/2006 | Lashinski et al. |
| 2006/0186143 A1* | 8/2006 | Argentine ............ 222/336 |
| 2008/0015687 A1 | 1/2008 | Lashinski et al. |

FOREIGN PATENT DOCUMENTS

| | | |
|---|---|---|
| EP | 0 656 215 A1 | 6/1995 |
| JP | 3-109404 A | 5/1991 |
| JP | 7-278203 A | 10/1995 |
| JP | 9-99052 A | 4/1997 |
| JP | 2000-502380 A | 2/2000 |
| WO | 97/22371 A1 | 6/1997 |
| WO | 01/44307 A2 | 6/2001 |
| WO | 2004/084703 A2 | 10/2004 |
| WO | 2006/091678 A1 | 8/2006 |

OTHER PUBLICATIONS

Mandai et al., "Direct thrombosis of aneurysms with cellulose acetate polymer Part I: Results of thrombosis in experimental aneurysms", J. Neurosurg., 1992, 77, pp. 497-500.

Matsushima et al., "Modification of E. coli Asparaginase With 2,4-Bis(O-Methoxypolyethylene Glycol)-6-Chloro-S-Triazine(Activated PEG2); Disappearance of Binding Ability Towards Anti-serum and Retention of Enzymic Activity", Chemistry Letters, 1980, pp. 773-776.

Nathan et al., "Copolymers of Lysine and Polyethylene Glycol: A New Family of Functionalized Drug Carriers", Bioconjugate Chem., 1993, vol. 4, pp. 54-62.

Sugawara et al., "Experimental Investigations Concerning a New Liquid Embolization Method: Combined Administration of Ethanol-estrogen and Polyvinyl Acetate", Neurol Med Chir (Tokyo), 1993, 33, pp. 71-76.

Taki et al., "A New Liquid Material for Embolization of Arteriovenous Malformations", AJNR, 1990, 11, pp. 163-168.

Vinters et al., "The histotoxicity of cyanoacrylates a selective review", Neuroradiology, 1985, 27, pp. 279-291.

European Search Report for EP 10 19 4236, Date of Completion of the Search Mar. 20, 2012.

Official Action issued for Japanese Application No. 2008-504235, dated Mar. 19, 2012 in Japanese with English translation of portions of Official Action.

Official Action issued for Japanese Application No. 2008-504235, dated Feb. 25, 2013 in Japanese with English translation of Official Action.

Official Action issued for Japanese Application 2013-174587, dated Sep. 22, 2014 in Japanese with English translation.

* cited by examiner

NON-DEGRADABLE, LOW SWELLING, WATER SOLUBLE RADIOPAQUE HYDROGEL POLYMER

CROSS-REFERENCES TO RELATED APPLICATIONS

This application is a continuation of U.S. application Ser. No. 11/097,467, filed Apr. 1, 2005, the entire contents of which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates to the development of hydrogel polymer compositions that are non-degradable, low-swelling and initially water soluble. More specifically, the hydrogel polymer compositions may be formed in situ and are useful as, e.g., embolic materials, bulking agents, and inflation or support media for certain types of medical devices. The present invention additionally includes a kit for preparing the hydrogel polymer compositions.

Hydrogel polymers are cross-linked hydrophilic macromolecules which have use in medical applications. While much progress has been made in such applications, further developments are needed to optimize the physical and mechanical properties of these materials for particular in vivo applications as described below.

One exemplary application for the hydrogel polymer materials discussed herein is as an inflation or support media for inflatable intraluminal grafts or stent grafts. Examples of such inflatable stent grafts are described in commonly owned U.S. Pat. No. 6,395,019 to Chobotov, pending U.S. patent application Ser. No. 10/384,103 to Kari et al. entitled "Kink-Resistant Endovascular Graft", filed Mar. 6, 2003, and U.S. patent application Ser. No. 10/327,711 to Chobotov et al., entitled "Advanced Endovascular Graft", filed Dec. 20, 2002, the entirety of each of which is incorporated herein by reference. These documents describe a stent graft in which additional structural integrity to the device may be achieved by the introduction of a polymeric fill material to channels and cuffs located on the graft portion so to act as a graft inflation and support medium.

Ideally, the inflation or support medium used in the stent grafts described above is biocompatible, has a cure time from about a few minutes to tens of minutes, exhibits minimal volumetric shrinking and swelling as it cures, exhibits long-term stability (preferably for at least ten years in vivo), poses as little an embolic risk as possible in the pre-cure state, and exhibits adequate mechanical properties, both in its pre- and post-cure states. For instance, such a material should have a relatively low viscosity before solidification or curing to facilitate the fill process into the stent graft.

Another application for the hydrogel polymers described herein is as a material for embolizing a body lumen such as a blood vessel or organ. Embolization, or the artificial blocking of fluid flow such as blood, may be used to treat a variety of maladies, including, by way of example only, controlling bleeding caused by trauma, preventing profuse blood loss during an operation requiring dissection of blood vessels, obliterating a portion of a whole organ having a tumor, blocking the blood flow into abnormal blood vessel structures such as aneurysms, arterio-venous malformations, arteriovenous fistulae, and blocking the passage of fluids or other materials through various body lumens. For such treatments, a variety of embolization technologies have been proposed, including for example mechanical means (including particulate technology), and liquid and semi-liquid technologies. The particular characteristics of such technologies (such as, e.g., the size of particles, radiopacity, viscosity, mechanism of occlusion, biological behavior and possible recanalization versus permanent occlusion, the means by which the material is delivered to the target body site, etc.), are factors used by the physician in determining the most suitable therapy for the indication to be treated.

Of the mechanical and particulate embolization technologies, the most prevalent include detachable balloons, macro- and microcoils, gelfoam and polyvinyl alcohol sponges (such as IVALON, manufactured and sold by Ivalon, Inc. of San Diego, Calif.), and microspheres. For example, one embolization technique uses platinum and stainless steel microcoils. However, significant expertise is required to choose a proper coil size for the malady prior to delivery. Moreover, many anatomical sites are not suitable for microcoils, and removal of microcoils has proved in certain circumstances difficult.

Liquid and semi-liquid embolic compositions include viscous occlusion gels, collagen suspensions, and cyanoacrylate (n-butyl and iso-butyl cyanoacrylates). Of these, cyanoacrylates have an advantage over other embolic compositions in their relative ease of delivery and in the fact that they are some of the only liquid embolic compositions currently available to physicians. However, the constituent cyanoacrylate polymers have the disadvantage of being biodegradable. Moreover, the degradation product, formaldehyde, is highly toxic to the neighboring tissues. See Vinters et al. "The histotoxicity of cyanoacrylate: A selective review", Neuroradiology, 1985; 27:279-291. Another disadvantage of cyanoacrylate materials is that the polymer will adhere to body tissues and to the tip of the catheter. Thus, physicians must retract the catheter immediately after injection of the cyanoacrylate embolic composition or risk adhesion of the cyanoacrylate and the catheter to tissue such as blood vessels.

Another class of liquid embolic compositions is precipitative materials, which was invented in the late 1980's. See Sugawara et al., "Experimental investigations concerning a new liquid embolization method: Combined administration of ethanol-estrogen and polyvinyl acetate", Neuro. Med. Chir. (Tokyo) 1993; 33:71-76; Taki et al., "A new liquid material for embolization of arterio-venous malformations", AJNR 1990; 11:163-168; Mandai et al., "Direct thrombosis of aneurysms with cellulous acetate polymer: Part I: Results of thrombosis in experimental aneurysms", J. Neurosurgery 1992; 77:497-500. These materials employ a different mechanism in forming synthetic emboli than do the cyanoacrylate materials. Cyanoacrylate glues are monomeric and rapidly polymerize upon contact with blood. On the other hand, precipitative materials are pre-polymerized chains that precipitate into an aggregate upon contact with blood.

Ideally, embolic material formed in situ is biocompatible, has a relatively short cure time from about a few seconds to a few minutes, exhibits minimal to moderate controllable swelling upon curing, exhibits long-term stability (preferably for at least ten years in vivo), and exhibits adequate mechanical properties, both in its pre- and post-cure state. For instance, such a material should have a relatively high viscosity before solidification or curing to facilitate safe and accurate delivery to the target site.

The hydrogel polymer materials described herein are also suitable for use in tissue bulking applications and more generally in inflatable devices suitable for implantation in a mammalian body, which devices are typically occlusive, such as those described variously in commonly owned copending U.S. patent application Ser. No. 10/461,853 to Stephens et al. entitled "Inflatable Implant", filed Jun. 13, 2003, the entirety of which is herein incorporated by reference. Such devices may be delivered to a specific site in the body in a low profile form and expanded after placement to occlude or to support some region, vessel, or duct in the body. Examples of tissue bulking applications include the treatment of sphincter deficiencies exhibited by, e.g., gastroesophageal reflux disease (GERD), urinary and fecal incontinence, augmentation of soft tissue, and certain orthopedic indications. Many of the ideal characteristics of embolic materials cited above are shared for these applications.

The majority of the hydrogel polymer materials in the literature contain ester, polyurethane or silicone groups. Even though such hydrogel polymers are relatively easy to manufacture either by free radical, anionic, or cationic polymerizations, they tend to degrade in the body. For example, most hydrogels containing ester bonds can be hydrolyzed under physiological pH.

Despite the advances made in the science of hydrogel polymer compositions for use in medical applications, there remains a need in the art for hydrogel polymers having improved physical and mechanical properties for particular in vivo applications as described herein.

BRIEF SUMMARY OF THE INVENTION

The present invention is for an in situ formed hydrogel polymer, comprising: (a) a first amount of a diamine; and (b) a second amount of a polyglycidyl ether; in which each of (a) and (b) are present in a mammal or in a medical device located in a mammal in an amount to produce an in situ formed hydrogel polymer that is biocompatible and has a cure time after mixing of from about 10 seconds to about 30 minutes. The volume of the hydrogel polymer of the invention swells less than 30 percent after curing and hydration.

The hydrogel composition may optionally comprise a radiopaque material. The radiopaque material is preferably selected from the group consisting of sodium iodide, potassium iodide, barium sulfate, Visipaque 320, Hypaque, Omnipaque 350 and Hexabrix.

In one embodiment, the hydrogel polymer comprises a polyglycidyl ether selected from the group consisting of trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A (PO)2 diglycidyl ether, hydroquinone diglycidyl ether, bisphenol S diglycidyl ether, terephthalic acid diglycidyl ester, and a mixture thereof.

In another embodiment, the hydrogel polymer comprises a diamine selected from the group consisting of (poly)alkylene glycol having amino or alkylamino termini selected from the group consisting of polyethylene glycol (400) diamine, di (3 aminopropyl) diethylene glycol r, polyoxypropylenediamine, polyetherdiamine, polyoxyethylenediamine, triethyleneglycol diamine, and a mixture thereof.

In yet another embodiment of the hydrogel polymer, the diamine component is hydrophilic and the polyglycidyl ether component is hydrophilic prior to curing. Alternatively, in the hydrogel polymer, the diamine component is hydrophilic and the polyglycidyl ether component is hydrophobic prior to curing. In another alternative, in the hydrogel polymer, the diamine component is hydrophobic and the polyglycidyl ether component is hydrophilic prior to curing.

The hydrogel polymer composition of the invention can be formed in situ in a mammal, or in a medical device located in the mammal, 1) in an intraluminal graft, 2) as an embolization device, 3) in an inflatable occlusion member, and 4) as a tissue bulking device. In one embodiment, the hydrogel polymer is form in situ in a mammal in an intraluminal graft. When the hydrogel polymer is formed in an intraluminal graft, the hydrogel polymer is, in one embodiment, formed from: (a) di-(3-aminopropyl)diethylene glycol; and (b) a mixture of polyethylene glycol glycidyl ether and trimethylolpropane triglycidyl ether.

The hydrogel polymer may also be formed in situ in a mammal or in a medical as an embolization device. When the hydrogel polymer is formed as an embolization device, the polymer is, in one embodiment, formed from: (a) a mixture of di-(3-aminopropyl)diethylene glycol and polyoxyethylenediamine; and (b) sorbitol polyglycidyl ether. In another embodiment, the hydrogel polymer that is formed in situ in an embolization device is formed from: (a) di-(3-aminopropyl) diethylene glycol; and (b) a mixture of pentaerythritol polyglycidyl ether and trimethylolpropane polyglycidyl ether.

The hydrogel polymer may also be formed in situ in a mammal or in a medical device located in the mammal as an inflatable occlusion member or as a tissue bulking device. In an inflatable occlusion member or as a tissue bulking device, the hydrogel polymer is, in one embodiment, formed from: (a) di-(3-aminopropyl)diethylene glycol; and (b) sorbitol polyglycidyl ether.

In yet another embodiment, the hydrogel polymer of the invention comprises a diamine component and a polyglycidyl component, in which the diamine component is present in an amount of between about 4 to about 20 weight percent of said polymer; and the polyglycidyl ether is present in an amount of between about 15 to about 60 weight percent of said polymer.

In yet another embodiment, the hydrogel polymer of the invention comprises a diamine component and a polyglycidyl component, in which the diamine component is present in an amount of between about 5 to about 15 weight percent of said polymer; and the polyglycidyl ether component is present in an amount of between about 25 to about 40 weight percent of the polymer.

In yet another embodiment, the hydrogel polymer of the invention comprises a diamine component and a polyglycidyl component, in which the diamine is di-(3-aminopropyl)diethylene glycol; the polyglycidyl ether is a mixture of polyethylene glycol glycidyl ether and trimethylolpropane triglycidyl ether; and the radiopaque material is selected from the group consisting of sodium iodide, potassium iodide, barium sulfate, Visipaque 320, Hypaque, Omnipaque 350 and Hexabrix.

In yet another embodiment, the hydrogel polymer of the invention comprises a diamine component and a polyglycidyl component, in which the diamine is di-(3-aminopropyl)diethylene glycol; the polyglycidyl ether is selected from the group consisting of sorbitol polyglycidyl ether and polyglycerol polyglycidyl ether; and the radiopaque material is selected from the group consisting of sodium iodide, potassium iodide, barium sulfate, Visipaque 320, Hypaque, Omnipaque 350 and Hexabrix.

In a certain embodiment of the hydrogel polymer, the diamine component is present in an amount of between about 7 to about 60 weight percent of the polymer; and the polyglycidyl ether is present in an amount of between about 7 to about 55 weight percent of the polymer.

In another embodiment of the hydrogel polymer, the diamine component is present in an amount of between about 10 to about 45 weight percent of said polymer; and the polyglycidyl ether is present in an amount of between about 14 to about 35 weight percent of said polymer.

In yet another embodiment of the hydrogel polymer, the diamine component is present in an amount of between about 5 to about 30 weight percent of said polymer; and the polyglycidyl ether is present in an amount of between about 40 to about 90 weight percent of said polymer.

In yet another embodiment of the hydrogel polymer, the diamine component is selected from the group consisting of di-(3-aminopropyl)diethylene glycol and polyoxyethylenediamine; the polyglycidyl ether is sorbitol polyglycidyl ether; and the radiopaque material is selected from the group consisting of sodium iodide, potassium iodide, barium sulfate, Visipaque 320, Hypaque, Omnipaque 350 and Hexabrix.

The present invention also provides for a kit for preparing an in situ hydrogel polymer composition comprising: (a) a container with a first amount of a diamine; (b) a container with a second amount of a polyglycidyl ether; and (c) optionally, a radiopaque material; and instructions for combining the materials present in each of said containers to produce the hydrogel polymer in situ in a mammal or in a medical device located in a mammal.

The present invention also sets forth a method of forming a hydrogel polymer composition comprising the steps of: (1) forming a mixture comprising a diamine and a polyglycidyl ether; (2) depositing said mixture in a mammal or into a medical device located in a mammal; and (3) allowing said mixture to cure and form said hydrogel polymer composition.

BRIEF DESCRIPTION OF THE DRAWINGS

Not Applicable.

DETAILED DESCRIPTION OF THE INVENTION

Abbreviations and Definitions

As used herein, the term "biocompatible" describes the characteristic of a polymer or other material to not have a toxic or injurious effect (i.e., does not cause infection or trigger an immune attack, or adversely affect the biological function in the expected conditions of use) in a mammalian biologic system.

As used herein, the term "radiopaque" or "contrast agent" is used to describe a material that is not transparent to X-rays or other forms of radiation. Radiopaque materials include but are not limited to sodium iodide, potassium iodide, barium sulfate, gold, tungsten, platinum, metrizamide, iopamidol, iohexol, iothalamate sodium, meglumine, Visipaque 320, Hypaque, Omnipaque 350, Hexabrix and tantalum powder).

As used herein, the term "embolization device" describes a substance that is introduced into a space, a cavity, or lumen of a blood vessel or other like passageway that partially or totally fills the space or cavity or partially or totally plugs the lumen. For example, an embolic composition can be used for occlusion of a vessel leading to a tumor or fibroid, occlusion of a vascular malformation, such as an arteriovenous malformation, occlusion of a left atrial appendage, as a filler for an aneurysm sac, as an endoleak sealant, as an arterial sealant, as a puncture sealant, or for occlusion of any other lumen such as, for example, a fallopian tube.

As used herein, the term "lumen" or "luminal" refers to various hollow organs or vessels of the body such as veins, arteries, intestines, fallopian tubes, trachea and the like. Lumen is also used to refer to the tubes present in a catheter system (i.e., "multi-lumen" catheter).

As used herein, the term "alkyl," by itself or as part of another substituent, means, unless otherwise stated, a straight or branched chain, or cyclic hydrocarbon radical, or combination thereof, which can be fully-saturated, mono- or polyunsaturated and can include di- and multivalent radicals, having the number of carbon atoms designated (i.e., $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds.

As used herein, the term "does not degrade" or "non-degradable" refers to the characteristic of a substance, such as a polymeric material, to resist being physically, chemically, or enzymatically decomposed (metabolized) into smaller molecular weight fragments, in a physiological environment to a degree that it impacts the function or biocompatibility of the material. Generally, a composition that does not degrade in an in vivo environment is one that is stable in aqueous pH 10 solution for at least 18 days which is equivalent to 10 years in vivo. The amount of degradation will typically be less than about 5% by weight, more preferably less than 4%, still more preferably less than 2%, even more preferably less than 1%, and most preferably less than about 0.5% by weight, relative to the overall weight of the polymer composition.

As used herein, the term "weight percent" refers to the mass of one component used in the formulation of a polymer composition divided by the total mass of the polymeric product and multiplied by 100%.

EMBODIMENTS OF THE INVENTION

I. Compositions

In one aspect, the present invention provides hydrogel polymer compositions that are biocompatible, pose no embolic risk, are non-degradable, and are stable in blood contact for >10 years. The gel compositions of the present invention are suitable for a variety of in vivo applications, including but not limited to, use in an intraluminal graft, as a luminal embolization device, in an inflatable occlusion member, and as a tissue bulking device, among others.

In its broadest concept, the hydrogel polymer compositions of the present invention are formed from at least two monomer components, i.e., a diamine and a polyglycidyl ether. The resulting gel composition of the invention does not contain a hydrolyzable group such as an ester group or amide group, among others. As a result, the present compositions exhibit increased stability in a physiological environment, and reduce the likelihood of breakdown in vivo.

Turning first to the diamine component of the present compositions, a suitable diamine monomer can be essentially any diamine compound in which each nitrogen atom is independently either an amino or an alkylamino group, and is sterically free to react with an epoxide moiety on a polyglycidyl ether. Typically, the diamine monomer has a molecular weight of between about 100 to about 2500; and in certain embodiments the diamine monomer is biocompatible. In one group of embodiments, the diamine is a polyoxyalkylene compound having amino or alkylamino termini. In a preferred embodiment, the polyoxyalkylene compound has amino termini. Suitable diamine monomers for the hydrogel polymer composition include, but are not limited to, polyethylene glycol diamine (also referred to as PEG-diamine or O,O'-Bis(2-aminoethyl)polyethylene glycol; CAS No. 24991-53-5), di-(3-aminopropyl) diethylene glycol (also referred to as O,O'-Bis(3-aminopropyl)diethylene glycol, diethylene glycol di-(3-aminopropyl)ether or 3-{2-[2-(3-Amino-propoxy)-ethoxy]ethoxy}-propylamine; CAS No. 4246-51-9), polyoxypropylenediamine (available from Huntsman Performance Products, Texas, USA; CAS No. 9406-10-0), polyetherdiamine (available from Huntsman Performance Products, Texas, USA; CAS No. 194673-87-5), polyoxyethylenediamine (available from Huntsman Performance Products, Texas, USA; CAS No. 65605-36-9), triethyleneglycol diamine (also known as 3,6-dioxa-octamethylenediamine; CAS No. 929-59-9), and mixtures thereof. In one embodiment, the diamine compound is di-(3-aminopropyl) diethylene glycol (available from Aldrich Chemical Company, Wisconsin, USA). In another embodiment, the diamine is a mixture of polyethylene glycol (400) diamine (available from Polypure Inc., Oslo, Norway; or from Tomah Inc., Wisconsin, USA) and di-(3-aminopropyl)diethylene glycol. In yet another embodiment, the diamine a mixture of polyoxyethylenediamine and di-(3-aminopropyl)diethylene glycol. Other suitable diamine monomers for the present composition will be apparent to those skilled in the art.

A second component for the gels of the present invention is a polyglycidyl ether. As used herein, the polyglycidyl ether monomer is any compound possessing at least two glycidyl ether functional groups, and preferably at least three glycidyl ether functional groups. In some embodiments, the polyglycidyl compound has at least two glycidyl ether groups and a molecular weight between 100 and 2000. Polyglycidyl ethers having two glycidyl ether groups are alternatively referred to in the art as diglycidyl ethers; while polyglycidyl ethers having three glycidyl groups are referred to as triglycidyl ethers. In most embodiments of the present invention, the polyglycidyl ether is biocompatible. Suitable polyglycidyl ethers for use in the composition include, but are not limited to, bis[4-(glycidyloxy)phenyl]methane (CAS No. 2095-03-6), 2,2-bis [4-(glycidyloxy)phenyl]propane (CAS No. 1675-54-3), bisphenol A propoxylate diglycidyl ether (CAS No. 106100-55-4), 1,4-butanediol diglycidyl ether (CAS No. 2425-79-8), 1,3-butanediol diglycidyl ether (CAS No. 3332-48-7), 1,4-cyclohexanedimethanol diglycidyl ether (CAS No. 14228-73-0), diethylene glycol diglycidyl ether (CAS No. 4206-61-5), ethylene glycol diglycidyl ether (CAS No. 2224-15-9 and CAS No. 72207-80-8), glycerol diglycidyl ether (CAS No. 27043-36-3), neopentyl glycol diglycidyl ether (CAS No. 17557-23-2), poly(dimethylsiloxane)-diglycidyl ether terminated (CAS No. 130167-23-6), polyethylene glycol diglycidyl ether (CAS No. 26403-72-5), poly(propylene glycol) diglycidyl ether (CAS No. 26142-30-3), resorcinol diglycidyl ether (CAS No. 101-90-6), sorbitol polyglycidyl ether (CAS No. 68412-01-1), polyglycerol polyglycidyl ether, pentaerythritol polyglycidyl ether (CAS No. 3126-63-4), diglycerol polyglycidyl ether (CAS No. 68134-62-3), glycerol polyglycidyl ether (CAS No. 25038-04-4), polyproylene glycol diglycidyl ether (CAS No. 26142-30-3), resorcinol diglycidyl ether (CAS No. 101-90-6), glycidyl ester ether of p-hydroxy benzoic acid (CAS No. 7042-93-5), neopentyl glycol diglycidyl ether (CAS No. 17557-23-2), 1,6-hexanediol diglycidyl ether (CAS No. 16096-31-4), bisphenol A (PO)$_2$ diglycidyl ether (available from Nagase ChemteX Corp., Osaka, Japan), o-phthalic acid diglycidyl ester (CAS No. 7195-45-4), hydroquinone diglycidyl ether (CAS No. 2425-01-6), bisphenol S diglycidyl ether (CAS No. 13410-58-7), terephthalic acid diglycidyl ester (CAS No. 7195-44-0), trimethylolpropane triglycidyl ether (CAS No. 30499-70-8), glycerol propoxylate triglycidyl ether (CAS No. 37237-76-6), trimethylolethane triglycidyl ether, triphenylolmethane triglycidyl ether (CAS No. 106253-69-4), as well as mixtures thereof. Other polyglycidyl ethers suitable for use in the present invention will be apparent to one skilled in the art.

In one embodiment, the polyglycidyl ether is a mixture of trimethylolpropane triglycidyl ether and polyethylene glycol diglycidyl ether (both available from Aldrich Chemical Company, Wisconsin, USA). In another embodiment, the polyglycidyl ether is a mixture of polyethylene glycol (600) diglycidyl ether (available from Polysciences, Inc., Pennsylvania, USA) and trimethylolpropane triglycidyl ether. In yet another embodiment, the polyglycidyl ether is a sorbitol polyglycidyl ether (available from Nagase ChemteX Corp., Osaka, Japan). In yet another embodiment, the polyglycidyl ether is a mixture of sorbitol polyglycidyl ether and polyglycerol glycidyl ether. In yet another embodiment, the polyglycidyl ether is a mixture of pentaerythritol polyglycidyl ether and trimethylolpropane polyglycidyl ether. One of skill in the art will appreciate that the properties of the resultant gel composition can be carefully controlled by varying the amount of polyglycidyl ether or combinations of polyglycidyl ethers to control the amount of cross-linking in the gel, the hydrophilic or hydrophobic character of the gel, as well as the cure time and viscosity of the pre-cure combination.

Optionally, the hydrogel polymer comprises at least one radiopaque material. Radiopaque materials suitable for the present invention include but are not limited to sodium iodide, potassium iodide, barium sulfate, gold, tungsten, platinum, Visipaque 320, Hypaque, Omnipaque 350, Hexabrix, metrizamide, iopamidol, iohexol, iothalamate sodium, meglumine, gold and tantalum powder. In some instances, it is preferable to use a blend of radiopaque material, as is in the case when it desired that the gel composition loses radiopacity over time. For instance, a blend of a soluble contrast agent such as an iodinated aqueous solution and an insoluble contrast agent such as barium sulfate can serve this purpose. The soluble contrast agent will leach out of the composition resulting in a progressive decrease in radiopacity of the composition over time.

The utility of the inventive gel compositions for many in vivo applications is attributed, in part, to the ease in which the mechanical properties of the pre- and post-cure gel composition can be modified, as noted above, simply through the judicious selection of the diamine and polyglycidyl ether components, and the curing conditions. For example, the cure rate is affected, in part, by the molecular weight of the monomer components used, and the concentration of the curing solution. In more detail, using a polyglycidyl ether having more glycidyl ether groups per monomer unit will provide a faster cure rate; using a higher concentration of monomer components in the pre-cure gel composition will provide a faster cure rate; and having a higher pH composition will provide a faster cure rate. Other methods of modifying the cure rate of the inventive composition will be readily apparent to a skilled artisan.

In another example, the firmness/hardness property of the final gel composition will be determined, in part, by the hydrophilic/hydrophobic balance of the monomer components. A higher proportion of hydrophobic monomers can provide a firmer gel composition. The firmness is also affected by the molecular weight of the monomer (i.e., a lower molecular weight provide a firmer gel), and the length of the monomer backbone of the polyglycidyl ether component (i.e., shorter polyglycidyl ether backbone provides a firmer gel). Other methods of modifying the hardness/firmness property of the final gel composition will be readily apparent to a skilled artisan.

In one embodiment, the composition comprises a hydrophilic diamine and a hydrophilic polyglycidyl ether. In another embodiment, the composition comprises a hydrophilic diamine and a hydrophobic polyglycidyl ether. In yet another embodiment, the composition comprises a hydrophobic diamine and a hydrophilic polyglycidyl ether.

The gel composition can optionally incorporate water or another aqueous fluid to result in increased volume (or swelling) of the final gel composition. The swelling of the final gel composition is inversely related to the firmness of the final gel. Depending of the proposed application, it is desirable that the inventive gel swells less than about 30 percent. In certain applications, such as in a embolization device, minimal swelling can be preferred.

The hydrogel polymer composition can optionally comprise various additives that can alter the mechanical or physical properties of the pre- or post-cure gel composition, e.g., to increase cure rate, to reduce viscosity, to introduce radiopacity. In one illustrative example, hydroxide can be added to the pre-cure gel mixture to catalyze rate of formation (cure rate) of the hydrogel polymer. In another illustrative example, fumed silica can be added to the pre-cure gel mixture to give it a thixotropic character desirable for certain embolization applications. Other comonomers and additives can be incorporated to the gel composition to alter the thermoresponsiveness, elasticity, adhesiveness and hydrophilicity of the final gel composition.

Optionally, the gel compositions of the present invention can be used to deliver drugs to the target site. The drugs can be mixed in or attached to the gel composition using a variety of methods. Some exemplary drugs and methods for attaching the drugs to the embolic composition are described in J. M. Harris, "Laboratory Synthesis of Polyethylene Glycol Derivatives," Journal of Macromolecular Science-Reviews in Macromolecular Chemistry, vol. C-25, No. 3, pp. 325-373, Jan. 1, 1985; J. M. Harris, Ed., "Biomedical and Biotechnical Applications of Poly(Ethylene Glycol) Chemistry", Plenum, New York, pp. 1-14, 1992; Greenwald et al., "Highly Water Soluble Taxol Derivatives: 7-Polyethylene Glycol Carbamates and Carbonates:", J. Org. Chem., vol. 60, No. 2, pp. 331-336, 1995, Matsushima et al., "Modification of *E. Coli Asparaginase* with 2,4-Bis(O-Methoxypolyethylene Glycol)-6-Chloro-S-Triazine (Activated PEG.sub.2); Disappearance of Binding Ability Towards Anti-Serum and Retention of Enzymic Activity," Chemistry Letters, pp. 773-776, 1980; and Nathan et al., "Copolymers of Lysine and Polyethylene Glycol: A New Family of Functionalized Drug Carriers," Bioconjugate Chem. 4, 54-62 (1993), each of which are incorporated herein by reference in its entirety.

As previously stated, the selection of monomer components for the gel composition will depend largely on the desired physical properties of the pre-cure monomer mixture and the final gel material, which is in turn dependent on its intended application in vivo. Specific uses for the gels of the present invention (including preferred monomers and amounts of monomers) are provided below as select embodiments of the invention.

Stent Graft or Intraluminal Graft:

The present gel compositions are useful in a polymeric stent-graft or intraluminal graft (e.g., as described in U.S. Pat. No. 6,395,019) located in a mammal for the purpose of inflating the channels and cuffs of the graft to conform to the morphology of the lumen, and to impart sufficient strength to the graft to resist to kinking. As used herein, the term "stent graft" interchangeably refers to inflatable intraluminal grafts as well as inflatable intralurninal stent grafts. For application in a stent graft or intraluminal device, it is preferable that the pre-cure gel composition comprise monomer components that are hydrophilic and biocompatible so as to minimize the embolic risk and toxicity that can result in the event of accidental release of the monomeric components in the bloodstream during addition of the pre-cure composition into the stent graft. Should accidental release occur, normal blood flow would then rapidly disperse the monomeric components and their concentration would fall below the level required to form a solid. Preferably, the pre-cure gel composition is soluble for at least 3 minutes in the bloodstream; more preferably for at least 5 minutes; even more preferably for at least 8 minutes or until just before cure.

In a stent graft application, it is less desirable for the gel composition to cure quickly as the pre-cure mixture should remain fluid in order to travel through a delivery tube into the stent graft. After the addition of the gel composition to the stent-graft, it is preferable for the graft to remain initially less rigid, so that the filled graft material can adjust and conform to the morphology of the vessel or lumen space. In one embodiment, the gel composition has a cure time from about 5 minutes to about 20 minutes. In another embodiment, the cure time is from about 10 to about 17 minutes. As stated above, it is beneficial for the pre-cure composition be a flowable solution that can be delivered through a delivery tube (e.g., catheter, syringe). In one embodiment, the viscosity of the pre-cure mixture is between about 10 to about 500 cp (centipoise). In another embodiment, the viscosity of the pre-cure mixture is between about 20 to about 100 cp, more preferably about 30 cp.

After curing, the gel composition maintains its biocompatibility and is stable in the event of contact with blood. The cured gel composition provides desirable mechanical properties such as, an elastic modulus between about 60 and about 500 psi, more preferably about 100 to about 400 psi, even more preferably about 200 to about 300 psi. Still further, the gel compositions that are used in stent-graft will typically be low swelling compositions and exhibit a volume change upon curing between about 0 to about 30 percent. As can be appreciated the pre-cure properties and post-cure properties of the gel composition described above are merely examples and should not limit the scope of the present invention.

The inventive gel composition in a stent graft typically show little or no volume change after curing. In one embodiment, the gel composition swells or shrinks less than about 20 percent after curing and hydration. In another embodiment, the gel composition swells or shrinks less than about 10 percent after curing and hydration. In yet another embodiment, the gel composition swells or shrinks less than 5 percent after curing and hydration. Low volume change of the gel mixture after curing and hydration is important in a stent graft material application. Excessive volume change of the hydrogel polymer after curing and hydration can adversely affect the strength of the graft material located inside the body lumen, and possibly jeopardize the safety of the mammal.

The hydrogel polymer can be comprised of any diamine or mixture of thereof; however, in one embodiment, the diamine or mixture thereof is a hydrophilic diamine. In another embodiment, the diamine monomer is selected from the group consisting of polyoxyethylenediamine, triethyleneglycol diamine, polyethylene glycol diamine, di-(3-aminopropyl)diethylene glycol, or a mixture thereof. It is desirable that the polyglycidyl ether component is also hydrophilic. In one embodiment, the polyglycidyl ether component is a mixture of a diglycidyl ether and a triglycidyl ether. In another embodiment the polyglycidyl ether component is mixture of polyethylene glycol diglycidyl ether and trimethylolpropane triglycidyl ether. In yet another embodiment, the polyethylene glycol diglycidyl ether is polyethylene glycol (600) diglycidyl ether. Furthermore, the hydrogel polymer can comprise a radiopaque material. In one embodiment, the radiopaque material is sodium iodide.

In one embodiment, the diamine is present in an amount of between about 4 to about 20 weight percent of the hydrogel polymer; and the polyglycidyl ether is present in an amount of between about 15 to about 60 weight percent of the hydrogel polymer. In another embodiment, diamine is present in an amount of between about 5 to about 15 weight percent of said polymer; and the polyglycidyl ether is present in an amount of between about 25 to about 40 weight percent of the hydrogel polymer.

In yet another embodiment, the diamine is di-(3-aminopropyl)diethylene glycol; the polyglycidyl ether is a mixture of polyethylene glycol diglycidyl ether and trimethylolpropane triglycidyl ether; and the radiopaque material is selected from the group consisting of sodium iodide, potassium iodide, barium sulfate, Visipaque 320, Hypaque, Omnipaque 350 and Hexabrix.

Embolic Compositions

In addition to the stent graft embodiments above, the present gel compositions can be constructed for use as an embolization device. Embolization devices block or obstruct flow through a body lumen. Numerous clinical applications exist for embolization of both vascular and nonvascular body lumens. The most prevalent uses for an embolization device include, but are not limited to, the neurological treatment of cerebral aneurysms, AVMs (arteriovenous malformations) and AVFs (arteriovenous fistula), and the peripheral treatment of uterine fibroids and hypervascular tumors. However, embolization devices are also useful in a variety of vascular or non-vascular body lumens or orifices, such as the esophagus, genital-urinary lumens, bronchial lumens, gastrointestinal lumens, hepatic lumens, ducts, aneurysms, varices, septal defects, fistulae, fallopian tubes, among others. Moreover, it should be appreciated that the gel composition as an embolization device can be used in conjunction with other components, such as endovascular grafts, stents, inflatable implants, fibers, coils, and the like. Other applications of embolization devices are described in co-pending U.S. patent application Ser. No. 11/031,311, titled "Methods, Materials, and Devices for Embolizing Body Lumens" to Whirley et al., the disclosure of which is incorporated herein by reference in its entirety.

For application in an embolic composition, it is preferable that the pre-cure gel composition is biocompatible and exhibit controllable solubility which is independent of the environment in which the embolic composition is delivered (e.g., in blood or other body fluid). More specifically, as the pre-cure gel mixture will be applied directly to the site for occlusion, in one aspect, it is be desirable for the pre-cure composition to be less soluble in blood or other body fluid and to remain relatively localized at the site of administration. In other embodiments, it is be desirable for the pre-cure gel composition to disperse through the vasculature as to provide a complete "cast" of a segment of the arterial tree after the gel composition cures (such as for a hypervascular tumor or an AVM), thereby reducing the opportunity for development of collateral perfusion. Typically, the present hydrogel polymer in an embolic application has a viscosity of 100 cp or higher, a controllable hydrophobicity and a faster cure rate than the compositions described above.

Applicants have found that for embolization applications it is desirable to increase the viscosity and hydrophobicity of the uncured material and thereby facilitate controlled placement without unintended embolization of distal vascular beds. This can be accomplished by reducing or eliminating saline or water from the gel composition. Reducing the saline and water prior to curing has been found to achieve the best viscosity for delivery into the body lumen, maximizes the degradation resistance of the cured polymer and maximizes the cohesiveness and hydrophobicity of the gel material.

Low viscosity formulations of the gel composition can also be used to deeply penetrate tumor vascular beds or other target embolization sites prior to curing of the composition. Occlusion balloons (such as a Swan-Ganz dual-lumen catheter or the EQUINOX™ Occlusion Balloon Catheter manufactured by Micro Therapeutics, Inc. of Irvine, Calif.) or other ancillary flow-blocking devices, such as brushes or other obstructive devices, some of which can be placed on a catheter or stent, such as those sometimes placed across a cerebral aneurysm to be embolized, can be used to prevent flow of the embolic composition beyond the target embolization site.

High viscosity and/or thixotropic (shear-thinning) formulations of these compositions can be used to limit the flow to the neighborhood of the delivery catheter and to facilitate the tendency of the gel composition to remain in the vicinity of the location in which it was delivered, sometimes even in the presence of substantial blood flow or other forces. Viscosity and/or thixotropy characteristics can be increased by adding bulking and/or thixotropic agents, such as fumed silica. The bulking agent can be added anytime during the formation of the gel composition, but is typically preloaded with one of the components, and preferably preloaded with the monomer/polymer or buffer solution.

Some examples of additives that are useful include, but are not limited to, sorbitol or fumed silica that partially or fully hydrates to form a thixotropic bulking agent, and the like. Desirable viscosities for the pre-cure gels range from about 5 centipoise (cP) for a low-viscosity formulation (such as might be used to deeply penetrate tissue in a hypervascular tumor) up to about 1000 cP or higher for a higher viscosity formulation (such as might be used to treat a sidewall cerebral aneurysm while minimizing the chance of flow disturbance to the embolic composition during the curing process). As can be appreciated, other embodiments of gels can have a higher or lower viscosity, and the gel composition is not limited to such viscosities as described above.

After curing, the embolic composition maintains its high biocompatibility and is stable in blood. The cured embolic composition provides desirable mechanical properties such as, a specific gravity between 1.15 to over 1.4, an elastic modulus between about 30 and about 500 psi, a strain to failure of about 25 percent to about 100 percent or more, a volume change upon curing between about 0 percent to about 200 percent or more, and a water content between less than 5 percent to greater than about 60 percent. In one embodiment, the volume change of the gel composition upon curing is less than about 20 percent. As can be appreciated the pre-cure properties and post-cure properties of the gel composition described above are merely examples and should not limit the scope of the embolic compositions of the present invention.

The gel composition of the present invention can be modified to provide other pre-cure and post-cure mechanical properties, as desired.

The hydrogel polymer can be comprised of any diamine or mixture of thereof; however, in one embodiment, the diamine or mixture thereof is a hydrophilic diamine. In another embodiment, the diamine is a hydrophobic diamine. The polyglycidyl ether can be hydrophilic or hydrophobic. In one embodiment, in the gel composition, a hydrophilic diamine will be paired with a less water-soluble, hydrophobic polyglycidyl ether. Alternatively, in another embodiment, in the gel composition, a more water-soluble hydrophilic polyglycidyl ether will be paired with a more hydrophobic diamine. The selection of suitable diamine and polyglycidyl ether components for the purpose of modify the mechanical properties of the pre-cure or the post-cure composition will be readily apparent to a skilled artisan. For example, to increase the firmness of the final gel composition, a polyglycidyl ether, such as a triglycidyl ether, which functions as a crosslinking agent, can be included in the composition. A skilled artisan will also recognize that the firmness of the formed gel composition will also be determined in part by the hydrophobic and hydrophilic balance of the monomer components, e.g., a higher hydrophobic percent provides a firmer hydrogel. In one embodiment, the diamine component is selected form the group consisting of di-(3-aminopropyl)diethylene glycol, polyoxyethylenediamine and, and a mixture thereof. In another embodiment, the polyglycidyl ether is selected from the group consisting of sorbitol polyglycidyl ether, polyglycerol polyglycidyl ether, trimethylolpropane triglycidyl ether, and mixtures thereof. In another preferred embodiment, the gel composition includes a radiopaque agent.

In one embodiment, the diamine is present in an amount of between about 7 to about 60 weight percent of the hydrogel polymer; and the polyglycidyl ether is present in an amount of between about 7 to about 55 weight percent of the hydrogel polymer. In another embodiment, diamine is present in an amount of between about 10 to about 45 weight percent of said polymer; and the polyglycidyl ether is present in an amount of between about 14 to about 35 weight percent of the hydrogel polymer.

In one embodiment, the diamine is present in an amount of between about 5 to about 30 weight percent of the hydrogel polymer; and the polyglycidyl ether is present in an amount of between about 40 to about 90 weight percent of the hydrogel polymer. In another embodiment, diamine is present in an amount of between about 50 to about 75 weight percent of said polymer; and the polyglycidyl ether is present in an amount of between about 10 to about 20 weight percent of the hydrogel polymer.

In yet another embodiment, the diamine is di-(3-aminopropyl)diethylene glycol; and the polyglycidyl ether is a mixture of pentaerythritol polyglycidyl ether and trimethylolpropane polyglycidyl ether; and the radiopaque material is sodium iodide.

In yet another embodiment, the diamine is a mixture of di-(3-aminopropyl)diethylene glycol and polyoxyethylenediamine; the polyglycidyl ether is sorbitol polyglycidyl ether; and the radiopaque material is selected from the group consisting of sodium iodide, potassium iodide, barium sulfate, Visipaque, Hypaque, Omnipaque, and Hexabrix.

Tissue Bulking Device and Inflatable Occlusion Member:

The present gel compositions are useful for in vivo application in an inflatable occlusion member and as a tissue bulking device. The gel composition are useful in vivo in a number of tissue bulking applications (e.g., aiding functionality of various organs or structures, such as assisting in closing a stricture (including restoring competence to sphincters to treat fecal or urinary incontinence or to treat gastroesophageal reflux disease (GERD)), augmentation of soft tissue in plastic or reconstructive surgery applications (e.g., chin or cheek reshaping), replacing or augmenting herniated or degenerated intervertebral disks. The pre-cure composition can be directly contacted with the tissue material; or can be introduced into an inflatable bag located in vivo. Alternatively, the pre-cure gel mixture can be added to an inflatable bag ex vivo, followed by placement of the bag inside the body.

It is preferable for the pre-cure gel composition to be biocompatible and exhibit controllable solubility which is independent of the environment in which the pre-cure mixture is delivered (e.g., in blood or other body fluid). More specifically, it is desirable for the pre-cure composition to be less soluble in blood or other body fluid and to remain relatively localized at the site of administration. Alternatively, in some embodiments, it is desirable for the pre-cure gel composition to diffuse to an in vivo site distal to the point of administration. Typically, the hydrogel polymer in a tissue bulking application has a viscosity of 100 cp or higher and controllable hydrophobicity. The solubility of the pre- and post-cure composition of the invention can be modified by any means known to one skilled in the art (e.g., through the choice of the hydrophobic or hydrophilic monomer components).

Preferably, the gel composition will have a cure time that is long enough to allow the gel composition to fill and conform to the cavity to which it is administered and/or long enough so that a medical professional can sculpt or otherwise shape the composition prior to the completion of the gelling process. In one embodiment, the gel composition has a cure time of from about 10 seconds to about 30 minutes depending on its intended site of administration. In another embodiment, the gel composition has a cure time of between about 30 seconds to about 2 minutes.

After curing, the gel composition remains biocompatible and is stable in blood. The cured polymer provides desirable mechanical properties such as, an elastic modulus between about 30 and about 500 psi, a strain to failure of about 25 percent to about 100 percent or more, a volume change upon curing between about 0 to about 30 percent or more, and a water content of about less than 60 percent. The volume change of the cured composition is preferably less than about 15 percent, and more preferably less than about 10 percent. As can be appreciated the pre-cure properties and post-cure properties of the gel composition in an embolic application described above are merely examples and should not limit the scope of the gel compositions of the invention. In one embodiment, the gel time is between about 30 seconds to about 25 minutes. In another embodiment, the gel time is between about 1 to about 3 minutes.

The hydrogel polymer can be prepared from any diamine or mixture thereof (as described generally above). However, in one embodiment, the diamine or mixture thereof is a hydrophilic diamine. In another embodiment, the diamine is a hydrophobic diamine. Similarly, the polyglycidyl ether can be hydrophilic or hydrophobic. In one embodiment, in the gel composition, a hydrophilic diamine will be paired with water-soluble, hydrophilic polyglycidyl ether. In another embodiment, the diamine is di-(3-aminopropyl)diethylene glycol. In another embodiment, the polyglycidyl ether is sorbitol polyglycidyl ether. In yet another embodiment, the gel composition comprises a radiopaque agent. In yet another embodiment, the radiopaque agent is Omnipaque, Visipaque, or a combination thereof. In yet another embodiment, the diamine is di-(3-aminopropyl)diethylene glycol; the polyglycidyl ether is sorbitol polyglycidyl ether; and the radiopaque material is a mixture of Visipaque and Omnipaque.

In one embodiment, the diamine is present in an amount of between about 4 to about 20 weight percent of the hydrogel polymer; and the polyglycidyl ether is present in an amount of between about 15 to about 60 weight percent of the hydrogel polymer. In another embodiment, diamine is present in an amount of between about 5 to about 15 weight percent of said polymer; and the polyglycidyl ether is present in an amount of between about 25 to about 40 weight percent of the hydrogel polymer.

Preparation of the Polymeric Hydrogels:

The gel composition can be made by combining the monomeric components in any order, as well as any additional monomers (comonomers) and other additives, under conditions suitable for formation of the polymer. The reaction is carried out in a suitable solvent; that being any solvent that dissolves the monomer components. For example, water, alcohols, such as ethanol or methanol, also carboxylic amides, such as dimethylformamide, dimethylsufoxide, and also a mixture thereof, are all solvents suitable for the reaction to make the hydrogel polymer. In one embodiment, the reaction is carried out in a substantially aqueous solution, e.g., in a basic sodium hydroxide solution (pH=7.4). Alternatively, the reaction can be carried out in under anhydrous conditions. Additionally, the skilled artisan will recognize that the mechanical properties of the final hydrogel product can be modified by changing at least the following variables: the choice of monomer components, the ratio of the monomer components (e.g. high or low molecular weight monomers), the concentration of the monomer(s), the pH of the reaction medium, the reaction time, and the rate of addition of the individual monomer components. For example, adding a triglycidyl ether in the composition, which can function as a crosslinking agent, can result in a gel material having increased hardness. Details are provided in the examples below to guide one of skill in the art in the preparation of the present gel compositions.

II. Method of Use

The hydrogel composition of the invention can be used in any medical application, in which the presence of a non-degradable, biocompatible hydrogel polymer is desired. More specifically, the present invention is particularly suited for applications that benefit from the in situ gelling characteristics. The present gel composition is especially useful in an inflatable occlusion member, an intraluminal graft, a tissue bulking device, and an embolization device.

In one aspect of the invention, the gel composition can be used in an in vivo environment, for example, as an intraluminal graft, such as, in a polymeric stent graft, as described in U.S. Pat. No. 6,395,019, the entirety of which is incorporated herein by reference, to improve the mechanical integrity of the stent graft. The '019 patent, describes that monomer components are added into the cuffs and channels of a stent graft, which upon curing, the final gel composition imparts additional strength to and conforms to the stent graft sealing cuffs.

In another aspect of the invention, the gel composition is also be useful as a tissue bulking (augmentation) device, such as, for augmentation of dermal support within intradermal or subcutaneous regions for the dermis, for breast implants, or for sphincter augmentation (i.e., for restoration of continence), among others. In this application, the pre-cure gel composition can be added to an inflatable bag located inside the body, or the pre-cure gel composition can be added to an inflatable bag ex vivo, which is then placed inside the body.

In yet another aspect of the invention, the gel composition can be formed directly on the tissue surface in an in vivo environment. Medical applications in which direct contact of body tissue with the inventive material is beneficial include, but are not limited to, as a puncture or wound sealant, and as an embolization device.

In one aspect, the gel composition can be used as an embolization device to form a plug for a variety of biological lumens. The compositions can be used to occlude blood vessels and other body lumens, such as, fallopian tubes and vas deferens, filling aneurysm sacs, and as arterial sealants. The embolization of blood vessels is useful for a number of reasons; to reduce the blood flow and encourage atrophy of tumors such as in the liver; to reduce blood flow and induce atrophy of uterine fibroids; for the treatment of vascular malformations, such as AVMs and AVFs; to seal endoleaks in aneurysm sacs; to stop uncontrolled bleeding; and to slow bleeding prior to surgery.

Method of Delivery:

The gel composition can be delivered to an in vivo site using any delivery devices generally known to those skilled in the art. The selection of the delivery device will depend on a number of factors, including the location of the in vivo site and whether a quick or slow curing gel is desired. In most cases, a catheter or syringe is used. In some cases, a multi-lumen catheter is used to deliver the hydrogel composition to the intended in vivo location, wherein the components of the composition are maintained in separate lumens until the time of administration. For example, a polyglycidyl ether component can be delivered in the first lumen, while the diamine compound is delivered through a second lumen. A third lumen can be used to deliver a contrast agent or other comonomers and/or additives to the in vivo site.

Alternatively, the components of the gel composition can be added to a multi-barrel syringe, wherein the barrels of the syringe are attached to a multi-pronged connector which is fitted to a spiral mixer nozzle (e.g., static mixer). As the components of the composition are pressed out of the syringe, they mix together in the nozzle and can be directly applied to tissue as needed in a relatively uniform, controlled manner. Additionally, the mixed components can be injected directly into tissue if the nozzle is further connected to a needle.

Injectable reaction mixture compositions also could be injected percutaneously by direct palpation, such as, for example, by placing a needle inside the vas deferens and occluding the same with the injected embolizing composition, thus rendering the patient infertile. The composition can be injected with fluoroscopic, sonographic, computed tomography, magnetic resonance imaging or other type of radiologic guidance. This would allow for placement or injection of the in situ formed hydrogel either by vascular access or percutaneous access to specific organs or other tissue regions in the body.

The gel composition can be added to a stent-graft in an in vivo environment. For example, one method for inflating a stent graft in such an environment is as follows: after the graft has been placed in the patient's body, and it is time to inflate the graft, the monomer components which are contained in a sterile kit having separate syringes for each monomer or mixtures thereof and also a timer, will be thoroughly mixed to begin the curing process. The contents are then transferred to one of the syringes and that syringe is attached to an autoinjector which is connected to a tube that is in turn connected to a biopolymer delivery tube located on the proximal end of the catheter. At the appropriate time, the autoinjector is turned on and the contents of the syringe is moved through the tube in the catheter that is connected on the distal end to a port on the graft where it enters the series of cuffs and channels to inflate the graft material.

Additional methods of delivering the composition to an in vivo site are also described in co-pending U.S. application Ser. No. 11/031,311

The following examples are meant to illustrate certain embodiments (e.g., stent graft fill, embolic composition, and tissue bulking compositions) of the invention and should not be construed in any way as limiting the invention.

EXAMPLES

Abbreviations Used
PEGGE: Polyethylene glycol glycidyl ether
TPTE: Trimethylolpropane triglycidyl ether
DCA or DCA-221: Di-(3-aminopropyl)diethylene glycol
cc: milliliters
DI: deionized water
1.5 N Gly-Gly: 1.5 N Glycine-glycine buffer
EX-411: pentaerythritol polyglycidyl ether
EX-321: trimethylpropane polyglycidyl ether (CAS No. 30499-70-8)
PBS: Phosphate Buffered Saline

Example 1

The following table shows formulations (1-7) that are useful, in one aspect of the invention, as stent graft fill material. These formulations can also find utility for other in vivo applications that require a hydrogel polymer having the properties as shown in Table 1.

TABLE 1

| Formulation | Material | Weight (g) | Wt % of Total | Mol Wt | # of mmoles | Gel Time | % Swelling | % Wt Gain | Notes/Observations |
|---|---|---|---|---|---|---|---|---|---|
| 1 | NaI (50%), pH 7.40 | 9.00 | 59.0 | | | 20 cc, 4.00 min; 1 cc, 12 min | 10.50% | 5.2 | Hard material |
| | PEGGE | 2.25 | 14.8 | 600 | 3.75 | | | | |
| | TPTE | 2.50 | 16.4 | 302 | 8.28 | | | | |
| | DCA221 | 1.50 | 9.8 | 222.00 | 6.76 | | | | |
| 2 | NaI (50%), pH 7.40 | 9.00 | 57.1 | | | 20 cc, 4 min; 1 cc, 12 min | 7 | 0.8 | Hard material |
| | PEGGE | 2.25 | 14.3 | 600 | 3.75 | | | | |
| | TPTE | 3.00 | 19.0 | 302 | 9.93 | | | | |
| | DCA221 | 1.50 | 9.5 | 222.00 | 6.76 | | | | |
| 3 | NaI (50%), pH 7.40 | 9.00 | 55.4 | | | 20 cc, 3.40 min; 1 cc, 11.20 min | 7 | 1.4 | Hard material |
| | PEGGE | 2.25 | 13.8 | 600 | 3.75 | | | | |
| | Epoxy Aldrich | 3.50 | 21.5 | 302 | 11.59 | | | | |
| | DCA221 | 1.50 | 9.2 | 222.00 | 6.76 | | | | |
| 4 | NaI (50%), pH 7.40 | 9.00 | 53.7 | | | 20 cc, 3.40 min; 1 cc, 11.20 min | 5.6 | 0.4 | Hard material |
| | PEGGE | 2.25 | 13.4 | 600 | 3.75 | | | | |
| | TPTE | 4.00 | 23.9 | 302 | 13.25 | | | | |
| | DCA221 | 1.50 | 9.0 | 222.00 | 6.76 | | | | |
| 5 | NaI (50%), pH 7.40 | 10.00 | 58.0 | | | 20 cc, 4.30 min; 1 cc, 11.40 min | 5.6 | 0 | Hard material |
| | PEGGE | 2.25 | 13.0 | 600 | 3.75 | | | | |
| | TPTE | 3.50 | 20.3 | 302 | 11.59 | | | | |
| | DCA221 | 1.50 | 8.7 | 222.00 | 6.76 | | | | |
| 6 | NaI (50%), pH 7.40 | 10.00 | 59.7 | | | 20 cc, 4.40 min; 1 cc, 12 min | 7 | 0 | Hard material |
| | PEGGE | 2.25 | 13.4 | 600 | 3.75 | | | | |
| | TPTE | 3.00 | 17.9 | 302 | 9.93 | | | | |
| | DCA221 | 1.50 | 9.0 | 222.00 | 6.76 | | | | |
| 7 | NaI (50%), pH 7.40 | 10.00 | 55.6 | | | 20 cc, 4.30 min; 1 cc, 11.40 min | 1.20% | −14% | Hard material |
| | PEGGE | 2.25 | 12.5 | 600 | 3.75 | | | | |
| | TPTE | 3.50 | 19.4 | 302 | 11.59 | | | | |
| | DCA221 | 1.50 | 8.3 | 222.00 | 6.76 | | | | |
| | PBS | 0.75 | 4.2 | | | | | | |

Example 2

The following table shows formulations (8-15) that are useful, in one aspect of the invention, as a stent graft fill material. These formulations can also find utility for other in vivo applications that require a hydrogel polymer having the properties as shown in Table 2.

TABLE 2

| Formulation | Material | Weight | Mol Wt | # of mmoles | Weight % Total | Epoxy/amine ratio | Gel Time 20 cc | Gel Times 1 cc | % Swell | Observations/Notes, all with 1 min mix |
|---|---|---|---|---|---|---|---|---|---|---|
| 8 | KI (100%) | 9.0 | | | 56.3 | 4.58 | 8.30 | 13.45 | 18 | Hard gel |
| | DCA | 0.5 | 221.0 | 2.26 | 3.1 | | | | | |
| | polyoxyethylene diamine | 3.0 | 2000.0 | 1.50 | 18.8 | | | | | |
| | Sorbitol polyglycidyl ether | 3.5 | 406.0 | 8.62 | 21.9 | | | | | |

TABLE 2-continued

| Formulation | Material | Weight | Mol Wt | # of mmoles | Weight % Total | Epoxy/amine ratio | Gel Time 20 cc | Gel Times 1 cc | % Swell | Observations/Notes, all with 1 min mix |
|---|---|---|---|---|---|---|---|---|---|---|
| 9 | KI (100%) | 9.0 | | | 62.1 | 2.62 | 15.00 | 15.30 | | Soft gel |
| | DCA | 0.5 | 221.0 | 2.26 | 3.4 | | | | | |
| | polyoxyethylene diamine | 3.0 | 2000.0 | 1.50 | 20.7 | | | | | |
| | Sorbitol polyglycidyl ether | 2.0 | 406.0 | 4.93 | 13.8 | | | | | |
| 10 | KI (100%) | 9.0 | | | 62.1 | 5.72 | 11.00 | 14.00 | 5 | soft gel |
| | DCA | 0.5 | 221.0 | 2.26 | 3.4 | | | | | |
| | polyoxyethylene diamine | 1.5 | 2000.0 | 0.75 | 10.3 | | | | | |
| | Sorbitol polyglycidyl ether | 3.5 | 406.0 | 8.62 | 24.1 | | | | | |
| 11 | KI (100%) | 9.0 | | | 69.2 | 3.27 | 14.30 | 14.30 | | soft gel |
| | DCA | 0.5 | 221.0 | 2.26 | 3.8 | | | | | |
| | polyoxyethylene diamine | 1.5 | 2000.0 | 0.75 | 11.5 | | | | | |
| | Sorbitol polyglycidyl ether | 2.0 | 406.0 | 4.93 | 15.4 | | | | | |
| 12 | KI (100%) | 7.0 | | | 50.0 | 4.58 | 9.00 | 13.00 | 21 | Hard gel |
| | DCA | 0.5 | 221.0 | 2.26 | 3.6 | | | | | |
| | polyoxyethylene diamine | 3.0 | 2000.0 | 1.50 | 21.4 | | | | | |
| | Sorbitol polyglycidyl ether | 3.5 | 406.0 | 8.62 | 25.0 | | | | | |
| 13 | KI (100%) | 7.0 | | | 56.0 | 2.62 | 12.30 | 14.00 | | soft gel |
| | DCA | 0.5 | 221.0 | 2.26 | 4.0 | | | | | |
| | polyoxyethylene diamine | 3.0 | 2000.0 | 1.50 | 24.0 | | | | | |
| | Sorbitol polyglycidyl ether | 2.0 | 406.0 | 4.93 | 16.0 | | | | | |
| 14 | KI (100%) | 7.0 | | | 56.0 | 5.72 | 7.30 | 12.30 | 10 | Hard gel |
| | DCA | 0.5 | 221.0 | 2.26 | 4.0 | | | | | |
| | Polyoxyethylene diamine | 1.5 | 2000.0 | 0.75 | 12.0 | | | | | |
| | Sorbitol polyglycidyl ether | 3.5 | 406.0 | 8.62 | 28.0 | | | | | |
| 15 | KI (100%) | 7.0 | | | 63.6 | 3.27 | 10.30 | 12.00 | 8 | Hard gel |
| | DCA | 0.5 | 221.0 | 2.26 | 4.5 | | | | | |
| | polyoxyethylene diamine | 1.5 | 2000.0 | 0.75 | 13.6 | | | | | |
| | Sorbitol polyglycidyl ether | 2.0 | 406.0 | 4.93 | 18.2 | | | | | |

Example 3

The following table shows formulations (16-24) that are useful, in one aspect of the invention, stent graft fill material. These formulations can also find utility for other in vivo applications that require a hydrogel polymer having the properties as shown in Table 3.

TABLE 3

| Formulation | Material | Weight | Mol Wt | # of mmoles | Weight % Total | Epoxy/amine ratio | Gel Time 20 cc | Gel Time 1 cc | % Swell |
|---|---|---|---|---|---|---|---|---|---|
| 16 | Omnipaque | 9.0 | | | 51.4 | 2.90 | 8.30 | 14:30 | 7.0% |
| | Buffer 1.5N pH 7.6 | 3.0 | | | 17.1 | | | | |
| | DCA221 | 1.5 | 221 | 6.79 | 8.6 | | | | |
| | Sorbitol polyglycidyl ether | 4.0 | 406 | 9.85 | 22.9 | | | | |
| 17 | Omnipaque | 10.0 | | | 50.0 | 3.99 | 11.00 | 14:20 | 5.6-7.0% |
| | Buffer 1.5N pH 7.6 | 3.0 | | | 15.0 | | | | |
| | DCA221 | 1.5 | 221 | 6.79 | 7.5 | | | | |
| | Sorbitol polyglycidyl ether | 5.5 | 406 | 13.55 | 27.5 | | | | |
| 18 | Visipaque | 12.0 | | | 60.0 | 3.63 | 11.13 | 12.56 | 2.80% |
| | DCA | 1.5 | 221.0 | 6.79 | 7.5 | | | | |
| | 1.5N Gly-Gly | 1.5 | | | 7.5 | | | | |
| | Sorbitol polyglycidyl ether | 5.0 | 406.0 | 12.32 | 25.0 | | | | |
| 19 | Visipaque | 11.0 | | | 59.5 | 2.90 | 13 | 14.3 | |
| | DCA | 1.5 | 221.0 | 6.79 | 8.1 | | | | |
| | 1.5N Gly-Gly | 2 | | | 10.8 | | | | |
| | Sorbitol polyglycidyl ether | 4.0 | 406.0 | 9.85 | 21.6 | | | | |

TABLE 3-continued

| Formulation | Material | Weight | Mol Wt | # of mmoles | Weight % Total | Epoxy/amine ratio | Gel Time 20 cc | Gel Time 1 cc | % Swell |
|---|---|---|---|---|---|---|---|---|---|
| 20 | Omnipaque | 10.0 | | | 47.6 | 3.99 | 11.00 | 14:20 | 5.6-7.0% |
| | Buffer 1.5N pH 7.6 | 3.0 | | | 14.3 | | | | |
| | DI | 1.0 | | | 4.8 | | | | |
| | DCA221 | 1.5 | 221 | 6.79 | 7.1 | | | | |
| | Sorbitol polyglycidyl ether | 5.5 | 406 | 13.55 | 26.2 | | | | |
| 21 | Omnipaque | 10.5 | | | 48.3 | 3.81 | 11.00 | 20.00 | 5.6-7.0% |
| | Buffer 1.5N pH 7.6 | 4.5 | | | 20.7 | | | | |
| | DCA221 | 1.5 | 221 | 6.79 | 6.9 | | | | |
| | Sorbitol polyglycidyl ether | 5.3 | 406 | 12.93 | 24.1 | | | | |
| 22 | Visipaque | 12.0 | | | 55.8 | 3.63 | 16 | 15.4 | 5.6-7.0% |
| | Di | 1.0 | | | 4.7 | | | | |
| | DCA | 1.5 | 221.0 | 6.79 | 7.0 | | | | |
| | 1.5N Gly-Gly | 2 | | | 9.3 | | | | |
| | Sorbitol polyglycidyl ether | 5.0 | 406.0 | 12.32 | 23.3 | | | | |
| 23 | Visipaque | 12.0 | | | 58.5 | 3.63 | 12.08 | 13.2 | 4% in graft |
| | DI | 0.5 | | | 2.4 | | | | |
| | DCA | 1.5 | 221.0 | 6.79 | 7.3 | | | | |
| | 1.5N Gly-Gly | 1.5 | | | 7.3 | | | | |
| | Sorbitol polyglycidyl ether | 5.0 | 406.0 | 12.32 | 24.4 | | | | |
| 24 | Visipaque | 11.4 | | | 55.6 | 3.63 | 11 | 14.3 | 6.00% |
| | Omnipaque | 0.6 | | | 2.9 | | | | |
| | DCA | 1.5 | 221.0 | 6.79 | 7.3 | | | | |
| | 1.5N Gly-Gly | 2 | | | 9.8 | | | | |
| | Sorbitol Polyglycidyl ether | 5.0 | 406.0 | 12.32 | 24.4 | | | | |

Example 4

The following table shows formulations (EM1-EM12) that are useful, in one aspect of the invention, as embolic materials. These formulations can also find utility for other in vivo applications that require a hydrogel polymer having the properties as shown in Table 4.

TABLE 4

| | | Components | Weight (g) | FW | mmoles | # of Reactive Sites | Weight % | Gel Time | Comments |
|---|---|---|---|---|---|---|---|---|---|
| EM-1 | 1 | EX-411 | 3.00 | 411 | 7.30 | 4 | 60.0 | 7:10 syringe | Some floating material. Soft, non-elastic, fractionating slug. |
| | | EX-321 | 0.50 | 321 | 1.56 | 3 | 10.0 | | |
| | 2 | NaI (100%) | 1.00 | | | | 20.0 | | |
| | 3 | DCA221 | 0.50 | 221 | 2.26 | 2 | 10.0 | | |
| | | Total | 5.00 | | | | 100.0 | | |
| EM-2 | 1 | EX-411 | 3.00 | 411 | 7.30 | 4 | 57.1 | 7:15 syringe | Floating material. Slightly firm slug |
| | | EX-321 | 0.25 | 321 | 0.78 | 3 | 4.8 | | |
| | 2 | NaI (100%) | 1.00 | | | | 19.0 | | |
| | 3 | DCA221 | 1.00 | 221 | 4.52 | 2 | 19.0 | | |
| | | Total | 5.25 | | | | 100.0 | | |
| EM-3 | 1 | EX-411 | 3.00 | 411 | 7.30 | 4 | 54.5 | 10:27 syringe | Floating material. Soft, wet, non-elastic slug. |
| | | EX-321 | 1.00 | 321 | 3.12 | 3 | 18.2 | | |
| | 2 | NaI (100%) | 1.00 | | | | 18.2 | | |
| | 3 | DCA221 | 0.50 | 221 | 2.26 | 2 | 9.1 | | |
| | | Total | 5.50 | | | | 100.0 | | |
| EM-4 | 1 | EX-411 | 3.00 | 411 | 7.30 | 4 | 50.0 | 6:12 syringe | Floating material. Very hard slug. |
| | | EX-321 | 1.00 | 321 | 3.12 | 3 | 16.7 | | |
| | 2 | NaI (100%) | 1.00 | | | | 16.7 | | |
| | 3 | DCA221 | 1.00 | 221 | 4.52 | 2 | 16.7 | | |
| | | Total | 6.00 | | | | 100.0 | | |
| EM-5 | 1 | EX-411 | 2.00 | 411 | 4.87 | 4 | 53.3 | 6:20 syringe | Floating material. Soft, elastic slug. |
| | | EX-321 | 0.25 | 321 | 0.78 | 3 | 6.7 | | |
| | 2 | NaI (100%) | 1.00 | | | | 26.7 | | |
| | 3 | DCA221 | 0.50 | 221 | 2.26 | 2 | 13.3 | | |
| | | Total | 3.75 | | | | 100.0 | | |

TABLE 4-continued

|  |  | Components | Weight (g) | FW | mmoles | # of Reactive Sites | Weight % | Gel Time | Comments |
|---|---|---|---|---|---|---|---|---|---|
| EM-6 | 1 | EX-411 | 2.00 | 411 | 4.87 | 4 | 47.1 | No cure time collected. Extended, cure- should have re- mixed | Floating material. Material in PBS does not demonstrate hydrophobicity. Slightly "grainy" texture. |
|  |  | EX-321 | 0.25 | 321 | 0.78 | 3 | 5.9 |  |  |
|  | 2 | NaI (100%) | 1.00 |  |  |  | 23.5 |  |  |
|  | 3 | DCA221 | 1.00 | 221 | 4.52 | 2 | 23.5 |  |  |
|  |  | Total | 4.25 |  |  |  | 100.0 |  |  |
| EM-7 | 1 | EX-411 | 2.00 | 411 | 4.87 | 4 | 44.4 | 6:20 syringe | Floating material. Soft, non-elastic, fractionating slug. |
|  |  | EX-321 | 1.00 | 321 | 3.12 | 3 | 22.2 |  |  |
|  | 2 | NaI (100%) | 1.00 |  |  |  | 22.2 |  |  |
|  | 3 | DCA22I | 0.50 | 221 | 2.26 | 2 | 11.1 |  |  |
|  |  | Total | 4.50 |  |  |  | 100.0 |  |  |
| EM-8 | 1 | EX-411 | 2.00 | 411 | 4.87 | 4 | 40.0 | 4:25 syringe At 4:00 drops became strings. | Very small amount floating material. Hot exotherm, ~75 C. Very hard slug. |
|  |  | EX-321 | 1.00 | 321 | 3.12 | 3 | 20.0 |  |  |
|  | 2 | NaI (100%) | 1.00 |  |  |  | 20.0 |  |  |
|  | 3 | DCA221 | 1.00 | 221 | 4.52 | 2 | 20.0 |  |  |
|  |  | Total | 5.00 |  |  |  | 100.0 |  |  |
| EM-9 | 1 | EX-411 | 2.50 | 411 | 6.08 | 4 | 62.5 | 10:5 syringe | Material in PBS cured at 8:00 |
|  |  | EX-321 | 0.20 | 321 | 0.62 | 3 | 5.0 |  |  |
|  | 2 | NaI (100%) | 1.00 |  |  |  | 25.0 |  |  |
|  | 3 | DCA221 | 0.30 | 221 | 1.36 | 2 | 7.5 |  |  |
|  |  | Total | 4.00 |  |  |  | 100.0 |  |  |
| EM-10 | 1 | EX-411 | 2.50 | 411 | 6.08 | 4 | 56.8 | 7:05 syringe | Drops became strings at 2:45. Soft, fractionating slug. |
|  |  | EX-321 | 0.40 | 321 | 1.25 | 3 | 9.1 |  |  |
|  | 2 | NaI (100%) | 1.10 |  |  |  | 25.0 |  |  |
|  | 3 | DCA221 | 0.40 | 221 | 1.81 | 2 | 9.1 |  |  |
|  |  | Total | 4.40 |  |  |  | 100.0 |  |  |
| EM-11 | 1 | EX-41 1 | 3.00 | 411 | 7.30 | 4 | 47.6 | 5:36 syringe Ice @ 37 C. cured at 7:36 | At 1:37, drops became strings. 5:50 material cure in PBS. Soft elastic, slug. |
|  |  | EX-321 | 1.00 | 321 | 3.12 | 3 | 15.9 |  |  |
|  | 2 | NaI (100%) | 1.70 |  |  |  | 27.0 |  |  |
|  | 3 | DCA221 | 0.60 | 221 | 2.71 | 2 | 9.5 |  |  |
|  |  | Total | 6.30 |  |  |  | 100.0 |  |  |
| EM-12 | 1 | EX-411 | 3.00 | 411 | 7.30 | 4 | 44.1 | 4:45 Syringe 1 cc @ 8:15 | Material cure in PBS @ 5:47 Injected Ice in blood |
|  |  | EX-321 | 1.50 | 321 | 4.67 | 3 | 22.1 |  |  |
|  | 2 | NaI (100%) | 1.70 |  |  |  | 25.0 |  |  |
|  | 3 | DCA221 | 0.60 | 221 | 2.71 | 2 | 8.8 |  |  |
|  |  |  | 6.80 |  |  |  | 100.0 |  |  |

Example 5

Formulation 7 was prepared according to the following experimental procedure.

The mixture of polyethylene glycol diglycidyl ether and trimethylolpropane triglycidyl ether is added to a single syringe. Di-(3-aminopropyl)ether diethylene glycol is added to a second syringe. The two syringes are connected using a delivery tube and ping-ponged mixed between syringes for approximately 20 seconds, with the syringed emptied fully every time with each stroke (approximately 1 stroke/second). A two milliliter sample stored in a 20 milliliter syringe cures in approximately 13 minutes at room temperature. This corresponds to an in vivo cure time of 13 minutes in an inflatable endovascular graft.

What is claimed is:

1. A biocompatible composition comprising a biocompatible solution comprising:
   (a) a diamine;
   (b) a polyglycidyl ether; and
   (c) a buffer solution comprising glycine-glycine;
   wherein said biocompatible solution does not form emboli in the blood;
   wherein said biocompatible solution forms a substantially water-insoluble hydrogel within about 20 minutes or less at a biocompatible temperature in the body; and
   wherein the polyglycidyl ether and diamine are present in a ratio such that biocompatibility is preserved.

2. The composition of claim 1, wherein said composition comprises a radiopaque material.

3. The composition of claim 1, wherein said polyglycidyl ether is selected from the group consisting of trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A (PO)$_2$ diglycidyl ether, hydroquinone diglycidyl ether, bisphenol S diglycidyl ether, terephthalic acid diglycidyl ester, and a mixture thereof.

4. The composition of claim 1, wherein said diamine is selected from the group consisting of (poly)alkylene glycol having amino or alkylamino termini selected from the group consisting of polyethylene glycol (400) diamine, di-(3-aminopropyl) diethylene glycol, polyoxypropylenediamine, polyetherdiamine, polyoxyethylenediamine, triethylenegylcol diamine, and a mixture thereof.

5. The composition of claim 1, wherein said diamine is hydrophilic and said polyglycidyl ether is hydrophilic prior to curing.

6. The composition of claim 1, wherein said diamine is hydrophilic and said polyglycidyl ether is hydrophobic prior to curing.

7. The composition of claim 1, wherein said diamine is hydrophobic and said polyglycidyl ether is hydrophilic prior to curing.

8. An implantable device comprising the composition of claim 1.

9. A biocompatible composition comprising a biocompatible solution comprising:
(a) di-(3-aminopropyl)diethylene glycol;
(b) sorbitol polyglycidyl ether; and
(c) a buffer solution comprising glycine-glycine;
wherein said composition forms a substantially water-insoluble hydrogel within about 20 minutes or less at a biocompatible temperature in the body.

10. An implantable device comprising the composition of claim 9.

11. The composition of claim 1, wherein said diamine is present in an amount of between about 4 to about 20 weight percent of said polymer; and said polyglycidyl ether is present in an amount of between about 15 to about 60 weight percent of said polymer.

12. The composition of claim 1, wherein said diamine is present in an amount of between about 5 to about 15 weight percent of said polymer; and said polyglycidyl ether is present in an amount of between about 25 to about 40 weight percent of said polymer.

13. The composition of claim 1, wherein said diamine is present in an amount of between about 7 to about 60 weight percent of said polymer; said polyglycidyl ether is present in an amount of between about 7 to about 55 weight percent of said polymer.

14. The composition of claim 1, wherein said diamine is present in an amount of between about 10 to about 45 weight percent of said polymer; said polyglycidyl ether is present in an amount of between about 14 to about 35 weight percent of said polymer.

15. The composition of claim 1, wherein said diamine is present in an amount of between about 5 to about 30 weight percent of said polymer; said polyglycidyl ether is present in an amount of between about 40 to about 90 weight percent of said polymer.

16. A kit for preparing the composition of claim 1 comprising:
(a) a container with a diamine;
(b) a container with a polyglycidyl ether;
(c) a buffer solution comprising glycine-glycine; and
instructions for combining the materials present in each of said containers to produce said hydrogel in situ in a mammal or in a medical device located in a mammal.

17. A method of forming a substantially water-insoluble hydrogel, said method comprising:
(1) forming a biocompatible composition comprising a biocompatible solution comprising a diamine, a polyglycidyl ether, and a buffer solution comprising glycine-glycine;
(2) depositing said composition in a mammal or into a medical device located in a mammal; and
(3) allowing said composition to cure and form said hydrogel;
wherein said solution is at least partially soluble in the blood and does not form emboli in the blood;
wherein said composition forms the hydrogel within about 20 minutes or less at a biocompatible temperature in the body; and
wherein the polyglycidyl ether and diamine are present in a ratio such that biocompatibility is preserved.

18. The composition of claim 1, wherein the ratio of polyglycidyl ether to diamine is from about 2.62 to about 5.72.

19. The composition of claim 1, wherein the ratio of polyglycidyl ether to diamine is from about 2.90 to about 4.58.

20. The composition of claim 1, wherein the ratio of polyglycidyl ether to diamine is from about 3.27 to about 3.81.

21. The composition of claim 1, wherein the diamine has a molecular weight of from between about 100 to about 2,500.

22. The composition of claim 1, wherein the polyglycidyl ether has a molecular weight from between 100 to 2000.

23. The composition of claim 1, wherein the composition has a cure time of from about 5 minutes to about 20 minutes.

24. The composition of claim 1, wherein the composition has a cure time of from about 10 minutes to about 17 minutes.

25. The composition of claim 1, wherein the diamine is di-(3-aminopropyl)diethylene glycol.

26. The composition of claim 25, wherein the polyglycidyl ether is sorbitol polyglycidyl ether.

27. The composition of claim 26, wherein the ratio of polyglycidyl ether to diamine is 3.63.

28. The composition of claim 1, wherein the composition cures in vivo.

29. The composition of claim 1, wherein the composition has a viscosity from about 5 centipoise to about 1000 centipoise prior to cure.

30. The composition of claim 1, wherein the hydrogel is a soft gel.

31. The implantable device of claim 8, wherein the implantable device is an inflatable implant.

32. The implantable device of claim 31, wherein the inflatable implant is selected from the group consisting of an inflatable intraluminal graft or an inflatable intraluminal stent-graft.

33. The implantable device of claim 8, wherein the implantable device is selected from the group consisting of an embolization device, an inflatable occlusion member, and a tissue bulking device.

34. The implantable device of claim 10, wherein the implantable device is an inflatable implant.

35. A biocompatible composition comprising a biocompatible solution comprising:
(a) di-(3-aminopropyl)diethylene glycol;
(b) sorbitol polygycidyl ether; and
(c) a buffer solution comprising glycine-glycine;
wherein the composition has a cure time from about 10 minutes to about 17 minutes at a biocompatible temperature in the body; and wherein the ratio of the sorbitol polyglycidyl ether to di-(3-aminopropyl)diethylene glycol is from about 3.27 to about 3.81.

36. A biocompatible composition comprising a biocompatible solution comprising:
(a) di-(3-aminopropyl)diethylene glycol;
(b) sorbitol polygycidyl ether; and
(c) a buffer solution comprising glycine-glycine;
wherein the composition has a cure time from about 10 minutes to about 17 minutes at a biocompatible temperature in the body; and wherein the ratio of the sorbitol polyglycidyl ether to di-(3-aminopropyl)diethylene glycol is from about 2.62 to about 2.90.

37. The composition of claim 2, wherein said radiopaque material is selected from the group consisting of sodium iodide, potassium iodide, barium sulfate, iodixanol, diatrizoate sodium, iohexol and ioxaglate salts.

38. The composition of claim 9, further comprising a radiopaque material.

39. The kit of claim 16, further comprising a radiopaque material.

40. The method of claim 17, wherein said biocompatible composition further comprises a radiopaque material.

41. The composition of claim 35, further comprising a radiopaque material.

42. The composition of claim 36, further comprising a radiopaque material.

* * * * *